US007810199B2

(12) United States Patent
Kressner

(10) Patent No.: US 7,810,199 B2
(45) **Date of Patent: *Oct. 12, 2010**

(54) ELECTRIC TOOTHBRUSH AND TOOTHBRUSH HEAD FOR THE SAME

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/404,885

(22) Filed: Mar. 16, 2009

(65) Prior Publication Data

US 2009/0217469 A1 Sep. 3, 2009

Related U.S. Application Data

(63) Continuation of application No. 10/507,845, filed as application No. PCT/EP02/12876 on Nov. 16, 2002, now Pat. No. 7,520,016.

(30) Foreign Application Priority Data

Mar. 15, 2002 (DE) ................................ 102 11 391

(51) Int. Cl.
*A61C 17/22* (2006.01)

(52) U.S. Cl. .......................... 15/22.1; 15/22.2; 15/22.4; 15/28

(58) Field of Classification Search .................. 15/22.1, 15/22.2, 22.4, 28; D4/101, 104, 105
See application file for complete search history.

(56) References Cited

U.S. PATENT DOCUMENTS 5,353,460 A * 10/1994 Bauman ..................... 15/22.1
5,467,495 A * 11/1995 Boland et al. .................. 15/28
5,524,312 A * 6/1996 Tan et al. ..................... 15/22.1
5,652,990 A * 8/1997 Driesen et al. ................. 15/28
5,842,245 A * 12/1998 Pai ............................ 15/22.1
6,021,538 A * 2/2000 Kressner et al. ................ 15/28
6,058,541 A * 5/2000 Masterman et al. ............ 15/28
6,237,178 B1 * 5/2001 Krammer et al. ............. 15/22.1
6,272,714 B2 * 8/2001 Beals ........................ 15/167.1
2002/0108194 A1 * 8/2002 Carlucci et al. ................ 15/28
2002/0138926 A1 * 10/2002 Brown et al. ................. 15/22.1
2003/0084524 A1 * 5/2003 Blaustein et al. ............. 15/22.1

FOREIGN PATENT DOCUMENTS

EP 765642 * 4/1997

* cited by examiner

*Primary Examiner*—Mark Spisich
(74) *Attorney, Agent, or Firm*—John P. Colbert; Vladimir Vitenberg

(57) ABSTRACT

A toothbrush head of an electric toothbrush, the toothbrush extending longitudinally and having a hand part, the toothbrush head including a drive rocker, a brush-head carrier coupled to the drive rocker, a main bristle carrier and an additional bristle carrier, both carriers bearing a bristle arrangement and moveably attached to the brush-head carrier and driven in oscillation by the drive rocker, and a drive-coupler affixed to at least one of the bristle carriers and coupled to the drive rocker. The head can include two separately mounted bristle carriers, supporting bristle arrangements, which are driven about different movement axes by the drive rocker to enhance the cleaning action of the toothbrush.

22 Claims, 13 Drawing Sheets

9 39 38 43 41 42 43 40 42 47 46 47 46 8 47 44 45 10 13 11

16
30
13
30
15
10
11

ELECTRIC TOOTHBRUSH AND TOOTHBRUSH HEAD FOR THE SAME

This is a continuation application (and claims the benefit of priority under 35 U.S.C. §120) of U.S. Ser. No. 10/507,845, filed Sep. 15, 2004 now U.S. Pat. No. 7,520,016, which is a 371 of PCT application serial no. PCT/EP02/12876, filed Nov. 16, 2002. Foreign priority is claimed 35 U.S.C. 119 from German Application 102 11 391.2, filed Mar. 15, 2002.

TECHNICAL FIELD

This description relates to a toothbrush head of an electric toothbrush which has a hand part with a drive, with a brush-head carrier, which can be connected to the hand part, and with a plurality of bristle carriers which each bear a bristle arrangement, are mounted in a moveable manner on the brush-head carrier and can be driven in oscillation by the drive, it being possible for the bristle carriers to be coupled to a drive transmitter by means of a drive coupling in each case.

BACKGROUND

U.S. Pat. No. 5,524,312 discloses an electric toothbrush, on the brush head of which are provided two separate bristle carriers which are driven by a common drive shaft. One bristle carrier executes an oscillating rotary movement about an axis which is perpendicular to the brush handle. The other bristle carrier is pivoted back and forth about an axis which is parallel to the brush handle. Although this bristle-carrier arrangement causes an active relative movement between the clusters of bristles, it is disadvantageous insofar as it is restricted to a specific drive mechanism, namely a transmission rod which reciprocates in the axial direction. The additional bristle carrier, which is arranged further rearwards in the direction of the hand part, requires a cylindrical underside with a special curved groove, in which an engagement protrusion of the longitudinally oscillating drive axis engages. In addition, the configuration of the clusters of bristles arranged on the two bristle carriers is not particularly suited for cleaning spaces between the teeth effectively.

SUMMARY

According to one aspect, a toothbrush head and a corresponding toothbrush provide straightforward, effective drive of the two bristle carriers.

The bristle carriers thus each have drive-coupling means by means of which they can be coupled to a common drive rocker of the drive, it being possible for said rocker to be rocked transversely to the longitudinal direction of the toothbrush. A better cleaning action can easily be achieved by the provision of two separately mounted bristle carriers, which are driven about different movement axes by a common drive rocker. The relative movement of the bristle arrangements mounted on the bristle carriers assists the cleaning movement, with the result that the cleaning action is not just produced by the person cleaning their teeth.

The drive rocker for driving the bristle carriers may be designed in different ways. According to one configuration of the invention, the bristle carriers may be coupled to a drive rocker which can be rocked in relation to a plurality of axes, describes a double-cone-shaped circulatory path and is assigned to the hand part of the toothbrush. As an alternative, it is also possible to provide a drive rocker which can be rocked in relation to just one axis and of which the rocking axis extends essentially perpendicularly to the longitudinal direction of the toothbrush, preferably such that the drive rocker can be rocked in a plane which contains the longitudinal axis of the toothbrush and is oriented perpendicularly to the main bristle direction defined by the clusters of bristles, i.e. is located essentially parallel to the planes defined by the bristle carriers. As an alternative, it is also possible for the drive rocker to rock in a plane which contains the main bristle direction and the longitudinal axis of the toothbrush, in particular when the bristle arrangements are to be driven with a picking movement. It is preferable, however, to provide the above described drive rocker which can be rocked in relation to a plurality of axes and describes a double-cone-shaped drive movement.

According to a development of the invention which is independent of a specific drive, the bristle carriers are each mounted on the brush-head carrier such that they can be moved about or along a movement axis in a direction transverse to the longitudinal direction of the toothbrush, each bristle carrier having its own movement axis, and these being spaced apart from one another. The toothbrush head is thus distinguished in that two bristle carriers which are mounted such that they can be moved about separate transverse axes are driven by a common drive-transmitter element, which can execute any desired drive movements. Irrespective of the actual design of the drive-transmitter element, such a toothbrush-head configuration has particular advantages in respect of effective teeth cleaning.

In particular, it is possible to provide two bristle carriers. A main bristle carrier, which may be arranged at that end of the brush-head carrier which is remote from the hand part of the toothbrush, is preferably mounted such that it can be rotated about an axis of rotation arranged essentially perpendicularly to the longitudinal direction of the toothbrush and essentially parallel to the main direction of the bristles provided on the main bristle carrier, and can be driven in oscillation by the drive rocker. The main bristle carrier may be of essentially plate-like design and have a circular contour. It can preferably be driven in a rotationally oscillating manner about its axis of symmetry. The rotationally oscillating drive movement may be combined, if appropriate, with a picking movement along the axis of rotation of the main bristle carrier, in order to achieve more thorough cleaning of the spaces between the teeth. It is possible, for this purpose, for the main bristle carrier to be mounted on the brush-head carrier such that it can be displaced in the direction of its axis of rotation.

Preferably provided alongside the main bristle carrier is an additional bristle carrier, which is arranged in the immediate vicinity behind the main bristle carrier, that is to say closer towards the hand part of the toothbrush. The additional bristle carrier may have different movement axes. According to a preferred configuration of the invention, the additional bristle carrier is mounted such that it can be pivoted about a pivot axis arranged essentially perpendicularly to the longitudinal direction of the toothbrush, and can be driven in oscillation by the drive rocker, which also drives the main bristle carrier.

According to one configuration of the invention, the pivot axis is arranged eccentrically in relation to the additional bristle carrier, or the bristle arrangement thereon, in order to achieve greater movement on a section of the bristle carrier which is located opposite the pivot axis. The pivot axis of the additional bristle carrier may be arranged approximately parallel to the main direction of the bristles, and thus parallel to the axis of rotation of the main bristle carrier. If the axis is arranged in the longitudinal direction of the toothbrush on a border section of the additional bristle carrier, the opposite border section of the additional bristle carrier executes a transversely reciprocating movement. It would also be possible, in principle, for the pivot axis to be arranged centrally in relation to the additional bristle carrier, with the result that the latter, in a manner similar to the main bristle carrier, itself rotates. It is preferable, however, for the pivot axis to be arranged, as described above, in particular at that end of the additional bristle carrier which is directed towards the hand part, with the result that the bristles which are adjacent to the main bristle carrier, and are fastened on the additional bristle carrier, can reciprocate transversely in the lateral direction and clean out the spaces between the teeth.

In an alternative development of the invention, it is possible for the pivot axis of the bristle carrier to be located essentially in the plane defined by the additional bristle carrier and to extend perpendicularly to the longitudinal direction of the toothbrush. The additional bristle carrier, accordingly, executes an up and down rocking movement, with the result that its clusters of bristles move up and down with picking action. This rocking axis of the additional bristle carrier can extend approximately centrally in relation to the longitudinal extent of the additional bristle carrier, in the longitudinal direction of the toothbrush, with the result that the rear end and the front end of the additional bristle carrier rock up and down in opposite directions. In an alternative configuration of the invention, it is also possible for the rocking axis of the additional bristle carrier to be displaced in the direction of one end of the additional bristle carrier. In particular, the additional bristle carrier may be mounted on the brush-head carrier such that it can be rocked about its end which is directed towards the hand part, with the result that the clusters of bristles which are adjacent to the main bristle carrier, and are fastened on the additional bristle carrier, execute an up and down picking movement. It is thus possible for the spaces between the teeth which are adjacent to tooth flanks treated by the bristle arrangement of the main bristle carrier to be cleaned particularly effectively.

It is not absolutely necessary, however, for the additional bristle carrier to be mounted in a pivotable manner. According to an advantageous configuration of the invention, it may be provided that the additional bristle carrier is mounted on the brush-head carrier such that it can be displaced in a translatory manner along a movement axis. The corresponding sliding guide of the additional bristle carrier preferably has a degree of freedom in a direction transverse to the longitudinal direction of the toothbrush.

In order for it to be possible, using the bristles arranged on the additional bristle carrier, to execute a picking movement in the longitudinal direction of the bristles, the translatory movement axis of the additional bristle carrier may be located essentially perpendicularly to the plane defined by the additional bristle carrier, i.e. essentially parallel to the main bristle direction defined by the bristles. As an alternative to this, the movement axis may be located transversely to the longitudinal direction of the toothbrush in the plane defined by the additional bristle carrier, with the result that the additional bristle carrier can be made to reciprocate transversely. It is thus possible for the bristles arranged on the additional bristle carrier to be moved in the direction of the spaces between the teeth and to clean these spaces out correspondingly.

The drive couplings between the two bristle carriers and the drive rocker are preferably designed as an articulated connection, each of which has an articulation axis in a direction transverse to the longitudinal direction of the toothbrush. Insofar as the drive rocker, rather than reciprocating in a translatory manner, executes a pivoting movement at its coupling points to the bristle carriers, it is possible for the articulated connection between the bristle carriers and the drive rocker to compensate for the corresponding angle offset.

In a development of the invention, the articulated connections between the drive-transmitter element and the bristle carriers, in addition to their articulation capability, have at least one further degree of freedom. In particular, the drive couplings of the bristle carriers are designed to transmit exclusively forces and movements transversely to the longitudinal direction of the toothbrush. No forces are transmitted in the longitudinal direction of the toothbrush. This makes it possible, on the one hand, to compensate for the relative movements, between the drive rocker and the bristle carriers, in the longitudinal direction of the toothbrush and, on the other hand, to exchange the toothbrush head in a straightforward manner. This is because the brush-head carrier preferably has releasable fastening means for fastening it on the hand part of the toothbrush, with the result that the brush-head carrier, together with the bristle carriers, can be removed from the hand part and/or positioned thereon. The drive couplings preferably have cutouts and/or engagement surfaces which, when the toothbrush head is plugged on, are introduced axially onto the drive-transmitter element on the hand part and/or the drive rocker. The drive couplings are preferably provided directly on the bristle carriers, i.e. the toothbrush head may be designed to be free of dedicated drive shafts, rockers or rods, the drive rocker, which is provided on the hand part, being introduced directly into a cutout in the additional bristle carrier and in the main bristle carrier and/or being brought into engagement with engagement surfaces of the additional bristle carrier and of the main bristle carrier, when the toothbrush head is plugged onto the hand part of the toothbrush.

In order to allow coupling to a drive rocker which can be rocked in relation to a plurality of axes and executes a double-cone-shaped drive movement, and in the process for the drive movement only to be partially transmitted to the bristle carriers, the articulated connection between the drive rocker and the bristle carriers may have a degree of freedom in a direction transverse to the longitudinal direction of the toothbrush. It is possible, in particular, for the connection between the drive rocker and the additional bristle carrier and/or the main bristle carrier to be designed to move freely in a direction transverse to the movement plane in which the respective bristle carrier is intended to move. Accordingly, the drive rocker, which moves in the form of a double cone, transmits just one component of its circulatory movement to the respective bristle carrier. If, for example, the additional bristle carrier is to be pivoted about an axis in a direction perpendicular to the additional bristle carrier, i.e. parallel to the bristles, the drive rocker may be seated in a longitudinal slot parallel to the bristle direction in the additional bristle carrier. The movement component transverse to the longitudinal direction of the bristles is transmitted to the bristle carrier, while the movement component of the drive rocker parallel to the longitudinal direction of the bristles is not transmitted. If, in contrast, the additional bristle carrier is to be rocked up and down, then the drive rocker may be seated in a transverse slot parallel to the bristle-carrier plane, with the result that the corresponding section is moved up and down, but the transversely reciprocating movement is not transmitted.

It is not necessary, however, for the drive rocker to be seated in a slot-like cutout in the additional bristle carrier. As an alternative, the additional bristle carrier may have, as drive coupling, a sliding surface which extends transversely to the longitudinal direction of the toothbrush and on which the drive rocker slides. It is preferably possible here to provide a prestressing device, for example in the form of a spring, which pushes the additional bristle carrier, by way of its sliding surface, onto the drive rocker and keeps it in engagement therewith. It is also possible, if appropriate, to dispense with such prestressing since, for example when the additional bristle carrier is to be rocked up and down with a picking movement, the additional bristle carrier is automatically pushed onto the drive rocker by the teeth-cleaning reaction forces.

If a drive rocker which circulates in the form of a double cone is provided, the engagement sliding surface of the additional bristle carrier may be of essentially planar design. In this case, the drive movement of the drive rocker has two mutually perpendicular components, with the result that the drive rocker slides back and forth on the sliding surface and, at the same time, pushes perpendicularly against the sliding surface and moves the bristle carrier correspondingly.

If, in contrast, a drive rocker which rocks in relation to one axis is provided, it is possible for the sliding surface to have a cam-like convexity in a direction transverse to the movement direction of the drive rocker. If the drive rocker moves in a reciprocating manner over the sliding surface, the cam-like convexity here produces the desired movement in the direction perpendicular to the reciprocating movement. If the drive rocker mounted on one axis rocks in the plane in which the bristle carrier is also to be moved, the engagement surface may be a straightforward bearing means.

In order to utilize the driven movement of the two bristle carriers, or of the bristle arrangements thereon, to better effect and to render teeth cleaning even more effective, a plurality of groups of clusters of bristles which are inclined in different directions may be arranged on the main bristle carrier and/or on the additional bristle carrier. It is possible here for the groups of clusters of bristles which are inclined in different directions to have different cross sections and/or to be designed with different properties, such as different stiffnesses, bristle lengths, bristle heights and the like. The clusters of bristles arranged on the main bristle carrier are preferably inclined in different directions to the clusters of bristles on the additional bristle carrier. According to one configuration of the invention, differently inclined clusters of bristles may be provided on each bristle carrier. It has proven expedient here to provide not just clusters of bristles with a circular cross section, but also clusters of bristles with a non-circular cross section, in particular with an elongate, oval or rectangular cross section.

In one embodiment, the main bristle carrier and/or on the additional bristle carrier include clusters of bristles having free working ends which are located at different heights above the bristle carriers to improve penetration into interstitial spaces between the teeth and enhance the cleaning action of the brush.

Further advantages, possible applications and advantageous features of the invention can be gathered from the following description of exemplary embodiments of the invention, which are illustrated in the figures of the drawing. In this case, all the features described or illustrated form, alone or in any desired expedient combination, the subject matter of the invention, irrespective of how they are summarized in the patent claims or how they relate back to preceding claims, and irrespective of how they are worded in the description or illustrated in the drawing.

Figure 1:
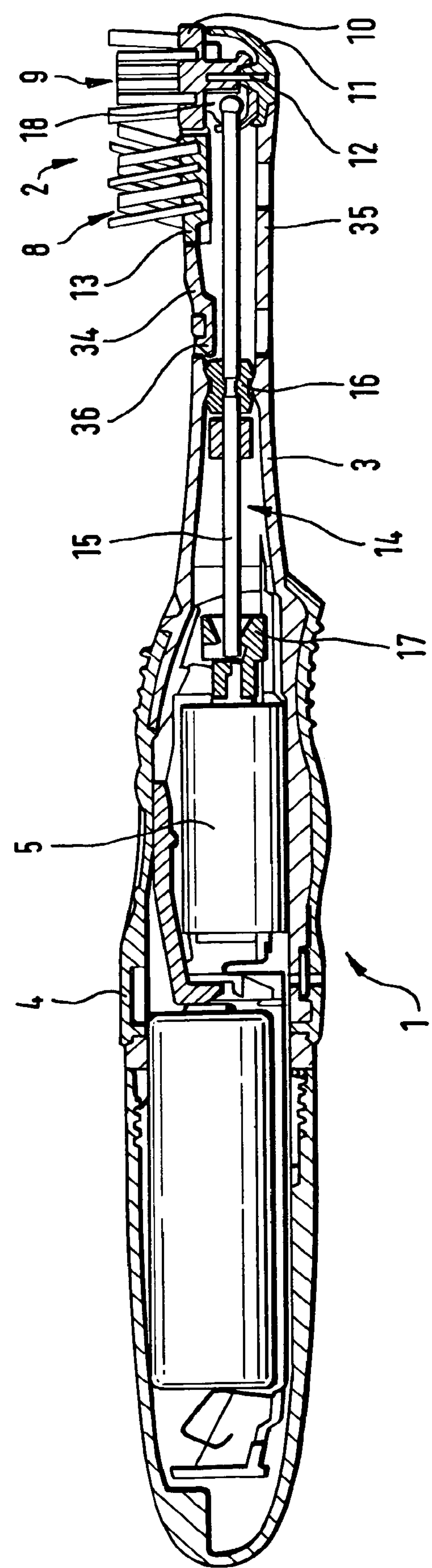
FIG. 1 shows a longitudinal section through an electric toothbrush with an exchangeable toothbrush head according to a first preferred configuration of the invention.

The toothbrush shown in FIG. 1 comprises a hand part 1 and a toothbrush head 2 which is seated on a brush tube 3, which forms an end of the hand part 1 or is connected thereto. The hand part 1 is formed by a toothbrush housing 4 in which a battery-accommodating compartment and a drive motor 5 are arranged axially one behind the other.

The brush head 2 has two bristle arrangements, namely a main bristle arrangement 9, which is located directly at the head end, and a rear, additional bristle arrangement 8, which is located in the immediate vicinity of the main bristle arrangement 9, on the side of the latter which is directed towards the hand part 1.

Figure 2:
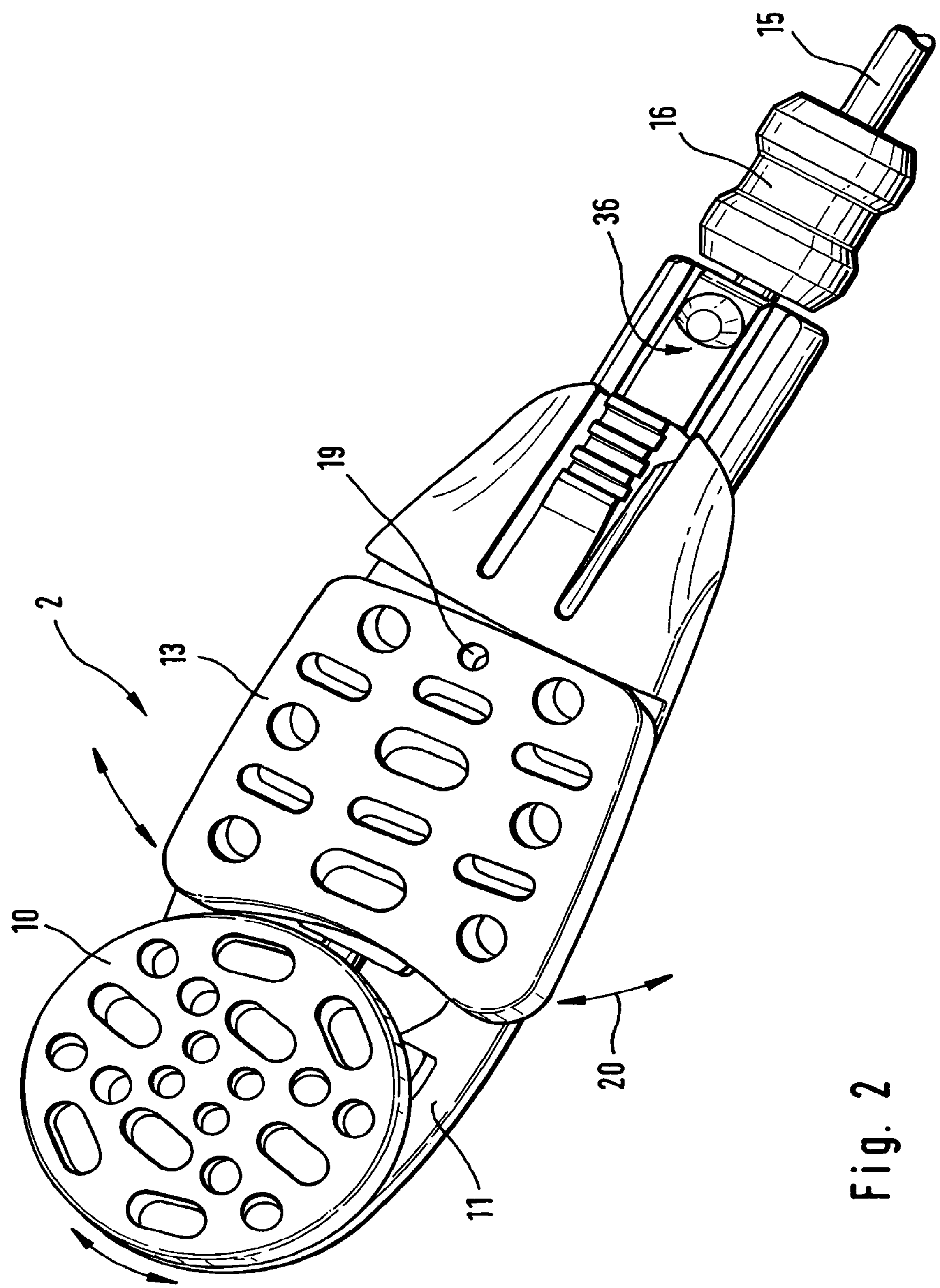
FIG. 2 shows a perspective plan view, in detail form, of the toothbrush head from FIG. 1, this showing two bristle carriers which are mounted in a moveable manner and are both mounted, and can be driven, such that they can be pivoted in each case about a pivot axis parallel to the main bristle direction.
Figure 13:
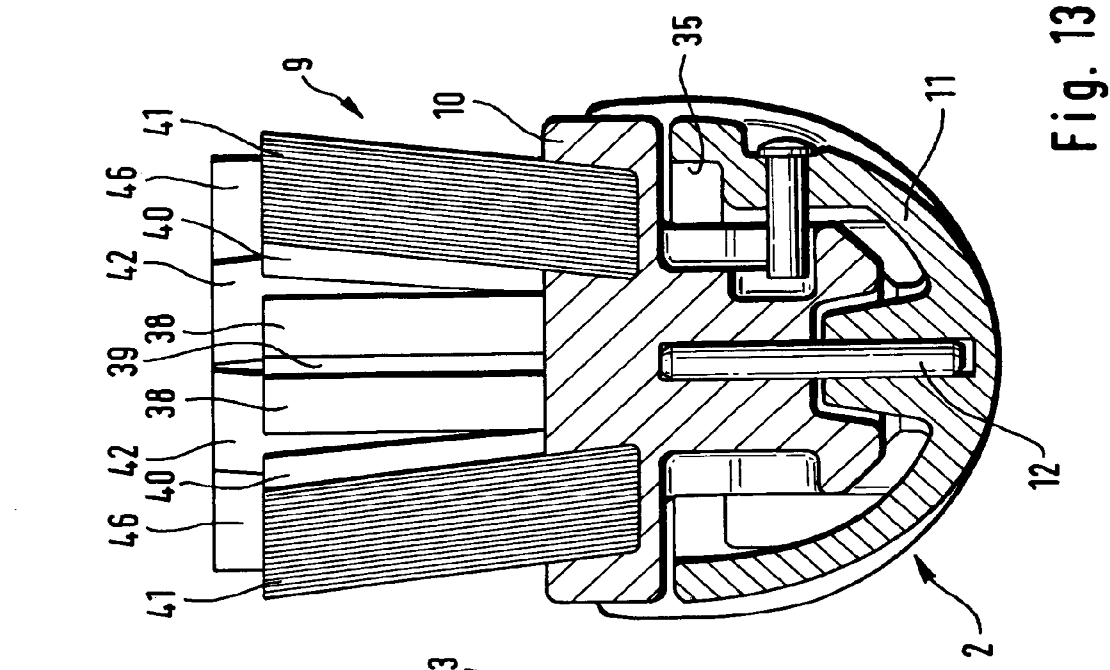
FIG. 13 shows a cross section through the axis of rotation of the main bristle carrier from FIG. 12 along line B-B in FIG. 14.

As FIG. 2 shows, the bristle arrangement, which is located at the head end, is borne by a main bristle carrier, which is designed approximately in the form of a circular plate in the direction of the bristle arrangement and is fastened on a brush-head carrier 11. As FIG. 13 shows, the bristle carrier 10 is fitted in a rotatable manner on an axis of rotation 12 which is anchored in the brush-head carrier 11 and extends, perpendicularly to the longitudinal axis of the toothbrush, approximately parallel to the main bristle direction of the bristle arrangement 9. The axis of rotation 12 forms the axis of symmetry of the plate-like bristle carrier 10.

The bristle carrier 10 is driven in rotational oscillation about the axis of rotation 12 by the motor 5, by means of a transmitter 14 in the form of a drive rocker 15. The drive rocker 15 is a rectilinear, essentially rigid metal rod and is mounted, between the motor in the hand part 1 and the bristle carrier 10 in the brush tube 3, in a bearing 16, which may be designed as an elastic bearing plug in the form of a ring or of a sleeve. The bearing 16 allows the drive rocker 15 to pivot about axes which are located in a plane perpendicular to the longitudinal direction of the toothbrush. The drive rocker 15 is driven by an eccentric 17 which is seated in a rotationally fixed manner on the motor shaft, which extends in the longitudinal direction of the toothbrush (cf FIG. 1). The drive rocker 15 here executes a double-cone-shaped tumbling or circulatory movement, the vertices of the two cones being located approximately in the region of the bearing 16. The two ends of the drive rocker 15 execute a circular-path movement in each case in a plane which is perpendicular to the longitudinal direction of the toothbrush.

Figure 14:
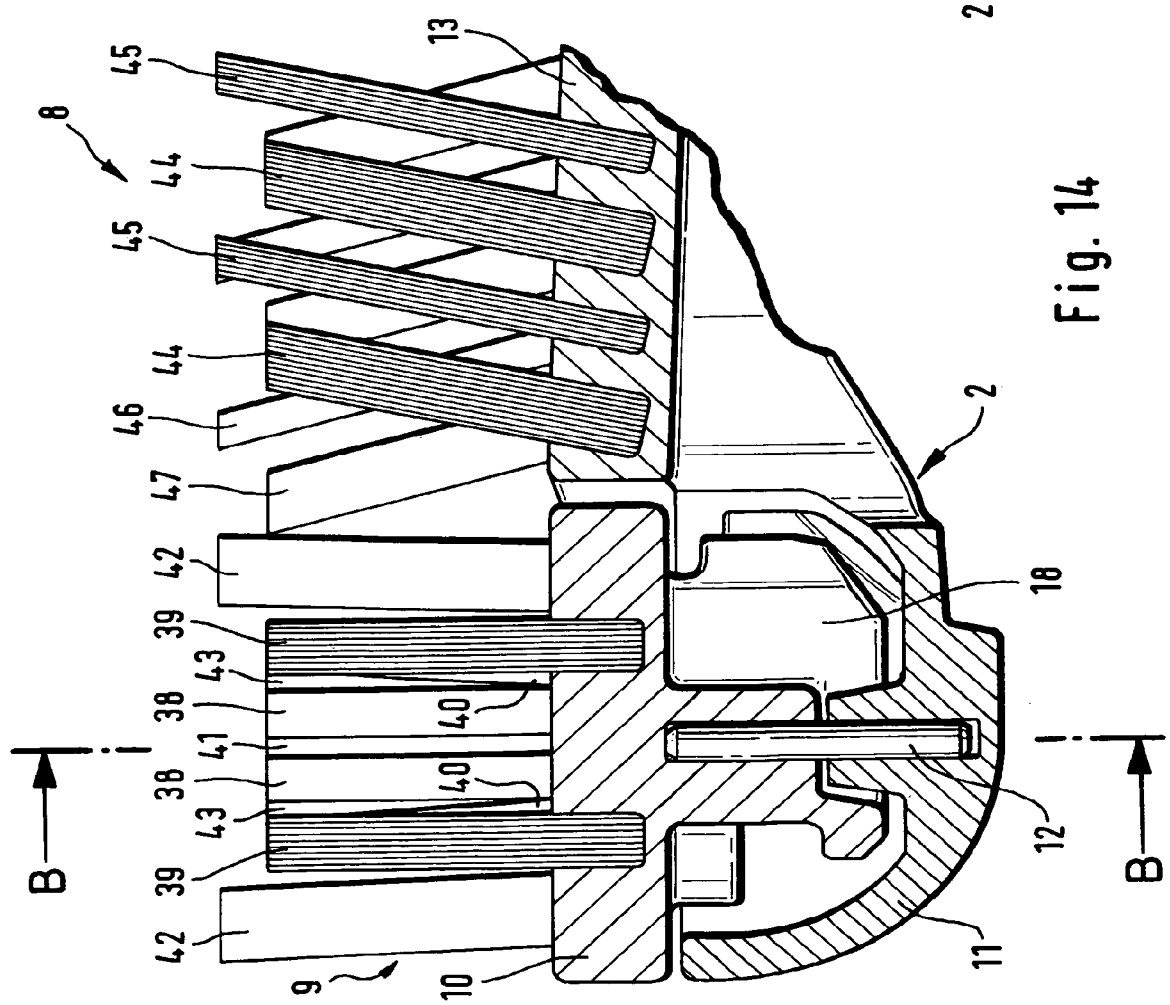
FIG. 14 shows a longitudinal section through the toothbrush head from FIG. 12.

That end of the drive rocker 15 which is directed towards the bristle carrier 10 is seated in a longitudinal-slot-like cutout 18 in the bristle carrier 10, said cutout being formed in a circumferential surface of the bristle carrier 10 which is directed towards the hand part 1 and extending essentially parallel to the axis of rotation 12 (cf. FIGS. 1 and 14). By virtue of the longitudinal-slot-like cutout, it is only the component of the drive movement of the drive rocker 15 in the direction transverse to the axis of rotation 12 which is transmitted to the bristle carrier 10. The up and down movement, i.e. the component of the circulatory drive movement parallel to the axis of rotation 12, is not transmitted since the drive rocker 15 can move freely parallel to the axis of rotation 12 in the cutout 18.

As FIG. 2 shows, the rear bristle arrangement 8, which is closer to the hand part 1, is borne by an approximately plate-like additional bristle carrier 13 which, like the main bristle carrier 10, is mounted in a moveable manner on the brush-head carrier 11 independently of the drive transmitter 14. As FIG. 2 shows, the additional bristle carrier 13 is mounted at its rear edge section, which is directed towards the hand part, such that it can be pivoted about a pivot axis 19 which extends essentially perpendicularly to the longitudinal direction of the toothbrush, or essentially parallel to the axis of rotation 12 of the bristle carrier 10, and perpendicularly to the plane defined by the additional bristle carrier 13. Accordingly, it is possible for the additional bristle carrier 13, in particular its section which is directed towards the main bristle carrier 10, to pivot transversely back and forth in the lateral direction, as the arrow 20 illustrates.

Figure 3:
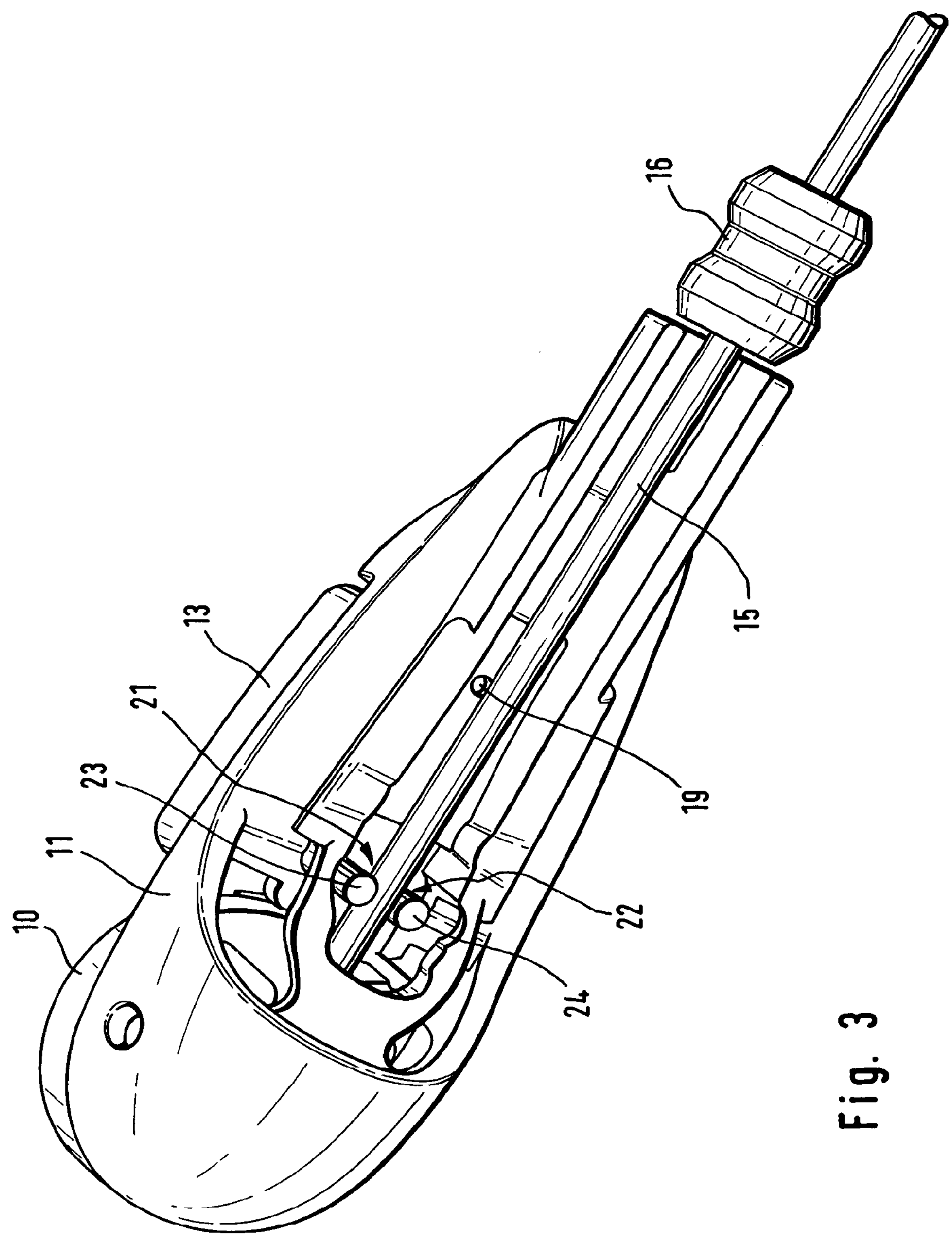
FIG. 3 shows a perspective view, in detail form, of the toothbrush head from FIG. 2 showing the drive mechanism and, in particular, the coupling of the rear, additional bristle carrier to a drive rocker.

In order to drive the additional bristle arrangement 8 in a rotationally oscillating manner about the pivot axis 19, the additional bristle carrier 13 is coupled to the drive rocker 15, which also drives the main bristle carrier 10. As FIG. 3 shows, there is provided, on the underside of the additional bristle carrier 13, a drive coupling 21 which comprises a longitudinal cutout 22 which is parallel to the pivot axis 19 and in which the drive rocker 15 is guided. In the configuration depicted, the longitudinal cutout 22 is defined by two post-like protrusions 23 and 24, between which the drive rocker 15 is guided. The protrusions 23, 24 extend essentially parallel to the pivot axis 19, with the result that the cutout defined between the protrusions 23 and 24, or the gap, likewise runs parallel to the pivot axis 19. Accordingly, in this case too, just one component of the circulating drive movement of the drive rocker 15 is transmitted, namely in the plane parallel to the longitudinal direction of the toothbrush, in the direction perpendicular to the pivot axis 19. The vertical component of the drive movement parallel to the plane of symmetry of the toothbrush is not transmitted, since the drive rocker can reciprocate freely in this direction in the longitudinal cutout 22 between the protrusions 23 and 24.

Alternative mountings for the additional bristle arrangement 8 or the additional bristle carrier 13 are shown in FIGS. 4 to 11. The toothbrush heads shown here are likewise envisaged for the toothbrush shown in FIG. 1 and otherwise correspond to the previously described toothbrush head so that, in this respect, you are referred to the description thereof and the same designations are used for corresponding components.

Figure 4:
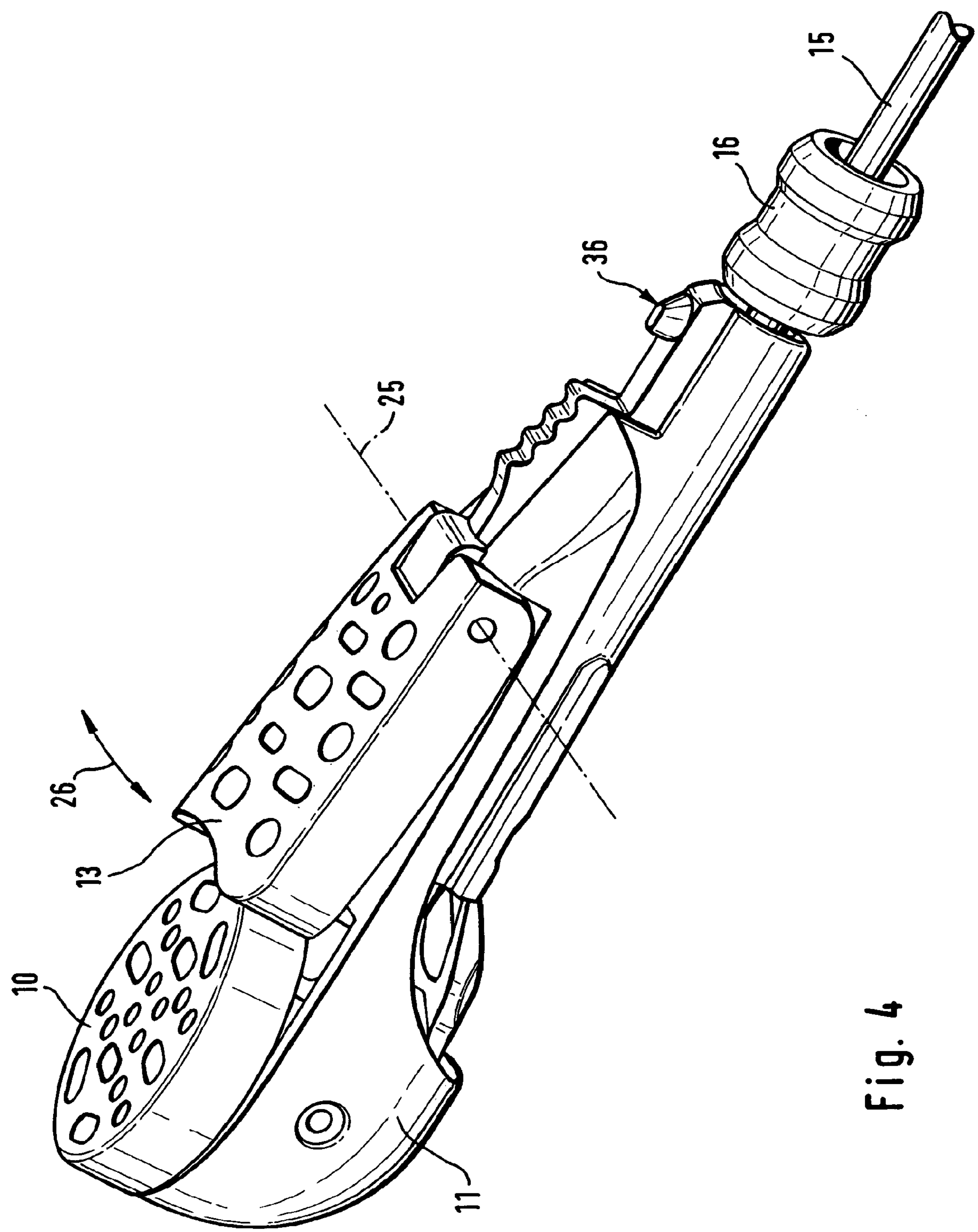
FIG. 4 shows a perspective view, in detail form, of a toothbrush head with two moveably mounted bristle carriers according to a further configuration of the invention, in which case the rear, additional bristle carrier is mounted, and can be driven, such that it can be rocked up and down about a transverse axis at its rear end section.

According to FIG. 4, the additional bristle carrier 13 is mounted on the brush-head carrier 11 such that it can be pivoted about a pivot axis 25 which extends essentially parallel to the plane defined by the additional bristle carrier 13, or transversely to the axis of rotation 12 of the bristle carrier 10, and runs transversely to the longitudinal direction of the toothbrush. The additional bristle carrier 13 here is mounted in a pivotable manner by way of its rear edge or end section, i.e. the one directed towards the hand part 1, with the result that it can execute an up and down rocking movement about the pivot axis 25. That section of the additional bristle carrier 13 which is directed towards the main bristle carrier 10 can rock up and down according to the arrow 26, with the result that the bristles of the additional bristle arrangement 8 execute a picking movement.

Figure 5:
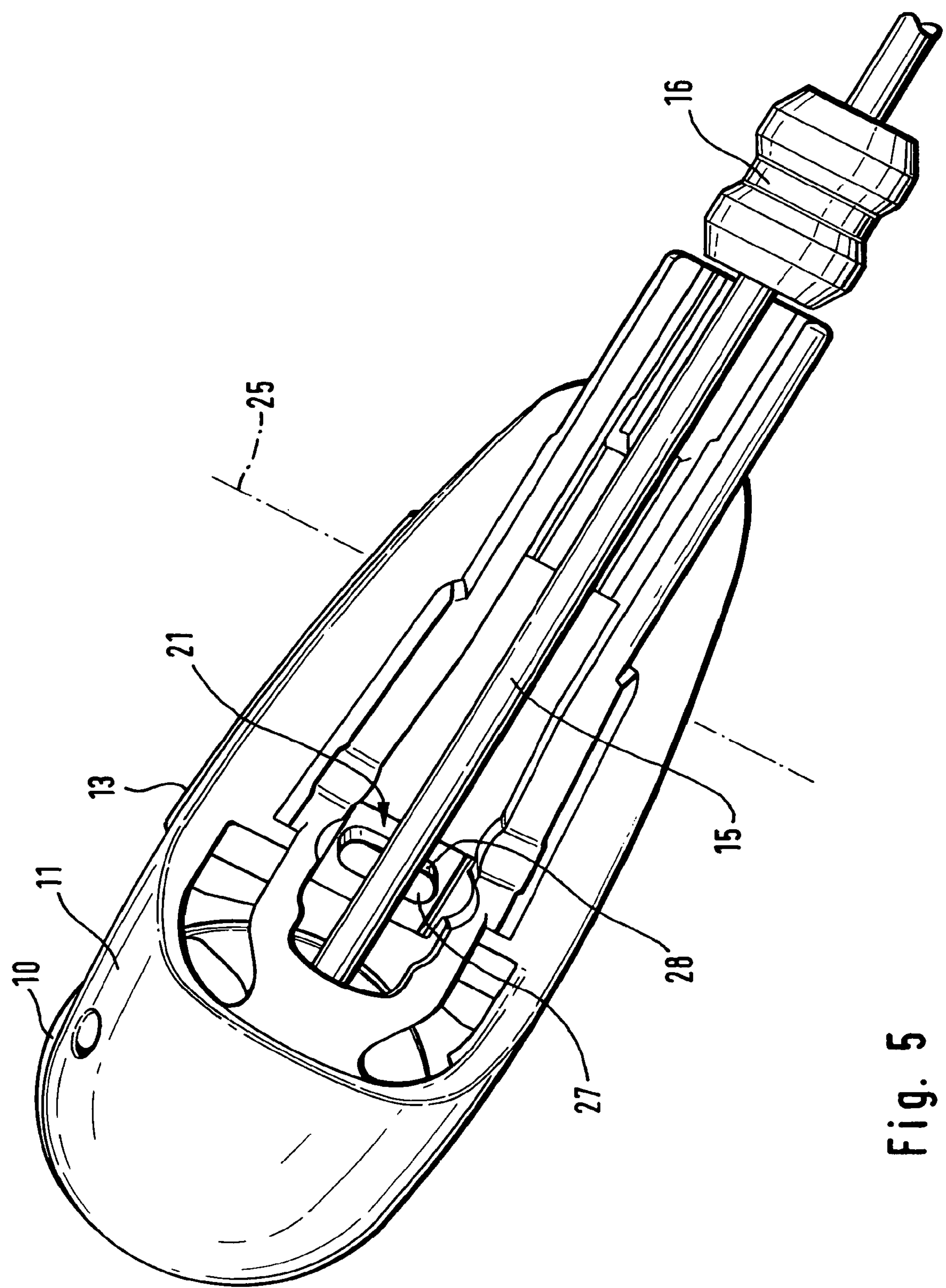
FIG. 5 shows a perspective view, in detail form, of the toothbrush head from FIG. 4 in a different viewing direction, this showing the drive mechanism for the two bristle carriers and, in particular, the coupling of the rear, additional bristle carrier to a drive rocker.

In order to drive the additional bristle carrier 13 in oscillation about the pivot axis 25, there is provided on its underside, as drive coupling, an engagement or sliding surface 27, by means of which it is seated on the drive rocker 15, which also drives the main bristle carrier 10. As FIG. 5 shows, the engagement or sliding surface 27 is formed by the end surface of an elongate tappet or protuberance 28 which extends transversely to the longitudinal direction of the toothbrush and projects in the direction of the drive rocker 15. The surface of the tappet 28 may be of essentially planar design. The circulating drive rocker moves transversely over the sliding surface 27, the vertical component of the circulating rocking movement being transmitted to the tappet or protuberance 28 and rocking the additional bristle carrier 13 up and down, the sliding surface 27 being kept in engagement with the drive rocker 15 by the teeth-cleaning reaction forces acting on the additional bristle arrangement. It is also possible here, if appropriate, to provide prestressing of the additional bristle carrier, for example by means of a spring, which pushes the additional bristle carrier against the drive rocker. As an alternative, it would also be possible, instead of providing the sliding surface 27, to provide a groove-like transverse cutout in a corresponding section of the additional bristle carrier 13, the drive rocker 15 being seated in said cutout, with the result that the drive rocker would push the additional bristle carrier upwards and pull it actively downwards. Such a transverse groove corresponds to the arrangement of two parallel sliding surfaces 27 between which the drive rocker 15 is guided.

Figure 6:
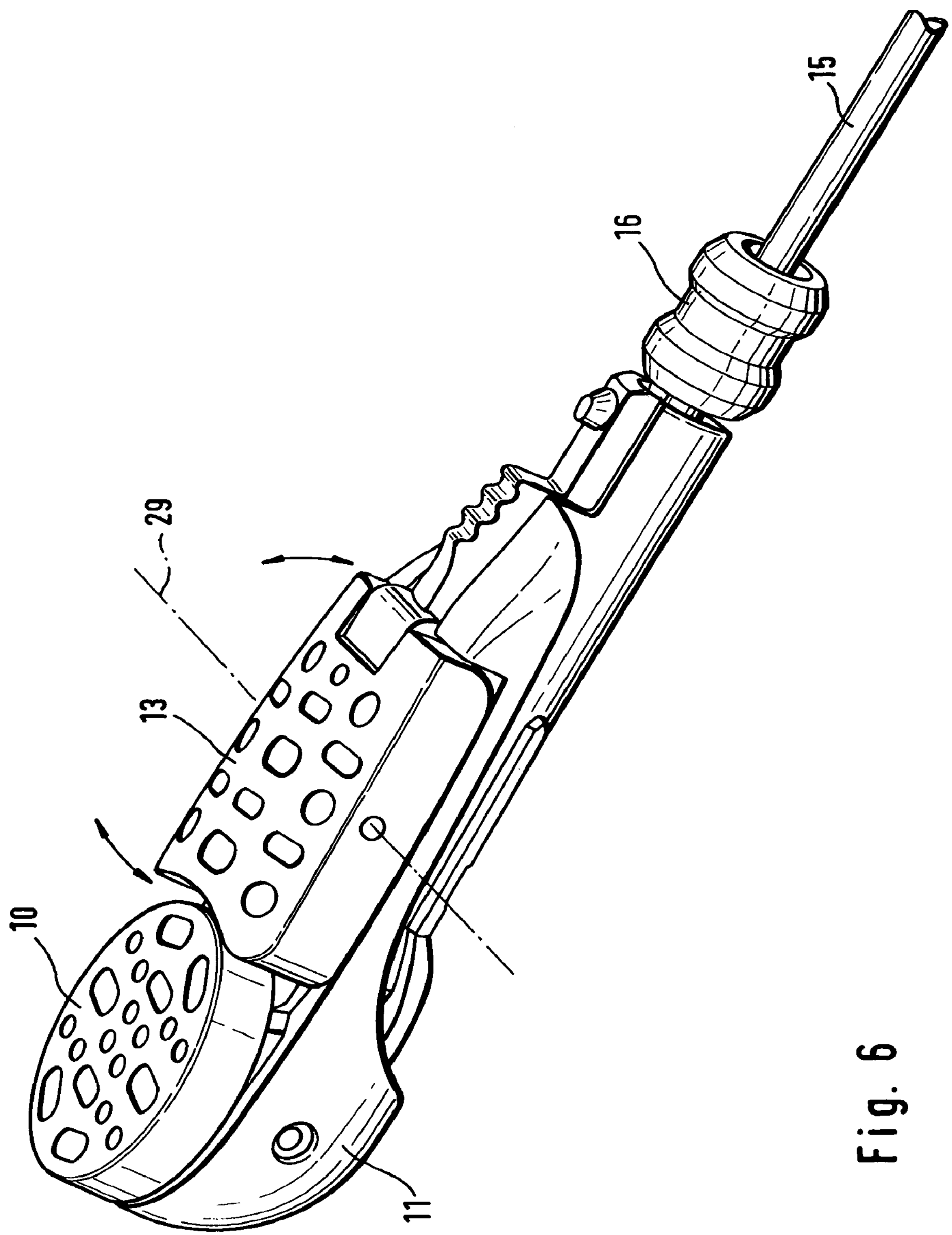
FIG. 6 shows a perspective view, in detail form, of a toothbrush head with two moveably mounted bristle carriers according to an alternative configuration of the invention, in which case the rear, additional bristle carrier is mounted approximately centrally such that it can be rocked about a transverse axis.
Figure 7:
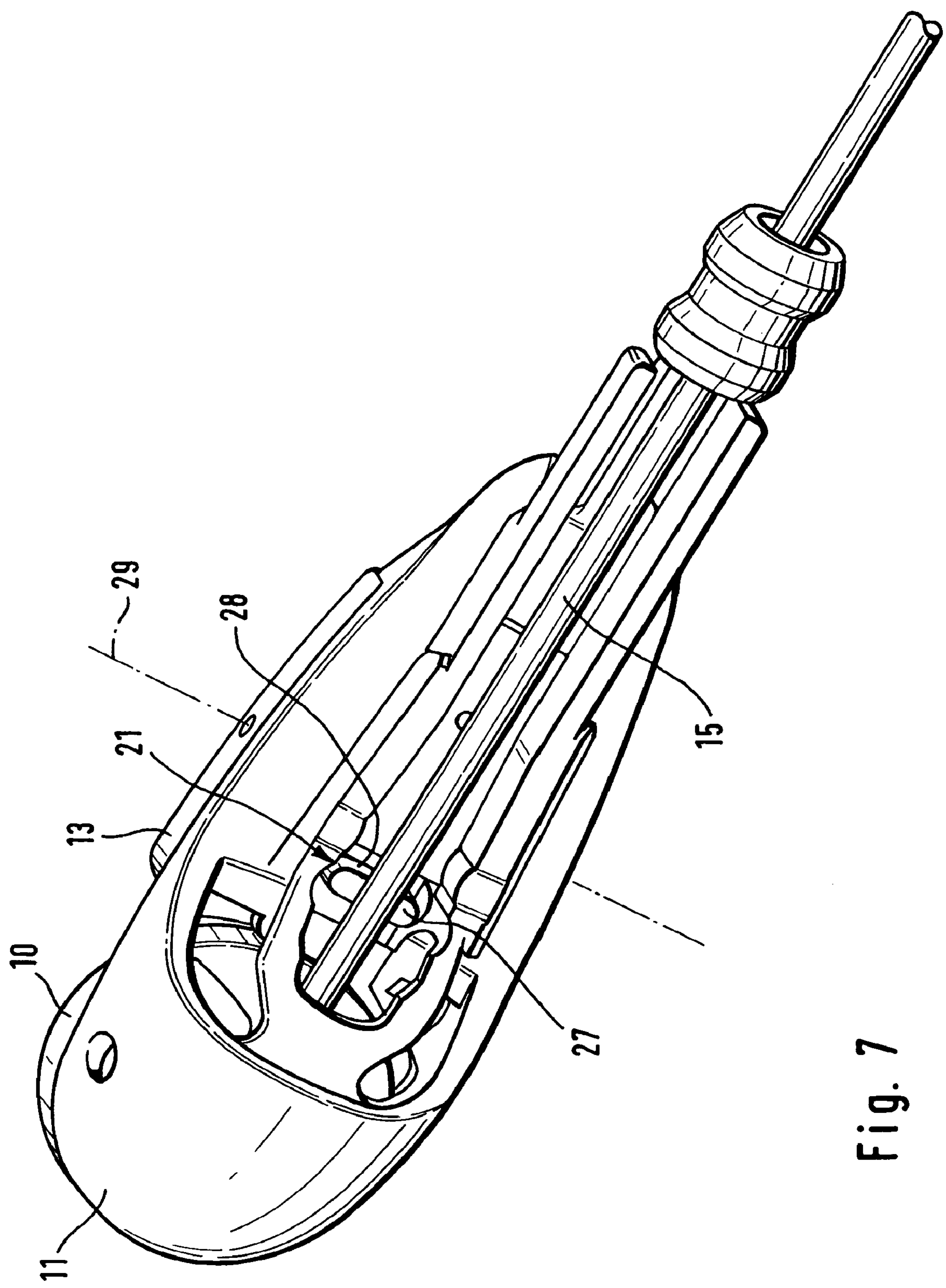
FIG. 7 shows a perspective view, in detail form, of the toothbrush head from FIG. 6 in a different viewing direction, this showing the drive mechanism for the two bristle carriers and, in particular, the coupling of the rear, additional bristle carrier to the drive rocker of the drive.

According to FIGS. 6 and 7, it is also possible for the additional bristle carrier 13 to be mounted approximately centrally about a transversely running pivot axis 29 in the manner of a rocker. As in the above described configuration, the pivot axis 29 extends, transversely to the longitudinal direction of the toothbrush, or to the axis of rotation 12 of the bristle carrier 10, approximately in the plane defined by the additional bristle carrier 13 or a plane parallel thereto, with the result that a section of the additional bristle carrier 13 which is directed towards the main bristle carrier 10 and an opposite section of the additional bristle carrier 13, which is directed towards the hand part 1, execute up and down rocking movements in opposite directions. The drive coupling of the additional bristle carrier may be formed, in a manner identical to the above described configuration according to FIGS. 4 and 5, by a sliding surface 27 which is provided on a tappet 28 and slides on the drive rocker 15. In so far as the teeth-cleaning reaction forces act on both sides of the pivot axis 29 in this configuration, a prestressing device which keeps the additional bristle carrier in engagement with the drive rocker 15 may be expedient. It is also possible here, if appropriate, to provide the above described positive guidance by means of a transverse groove, in which the drive rocker is seated.

Figure 8:
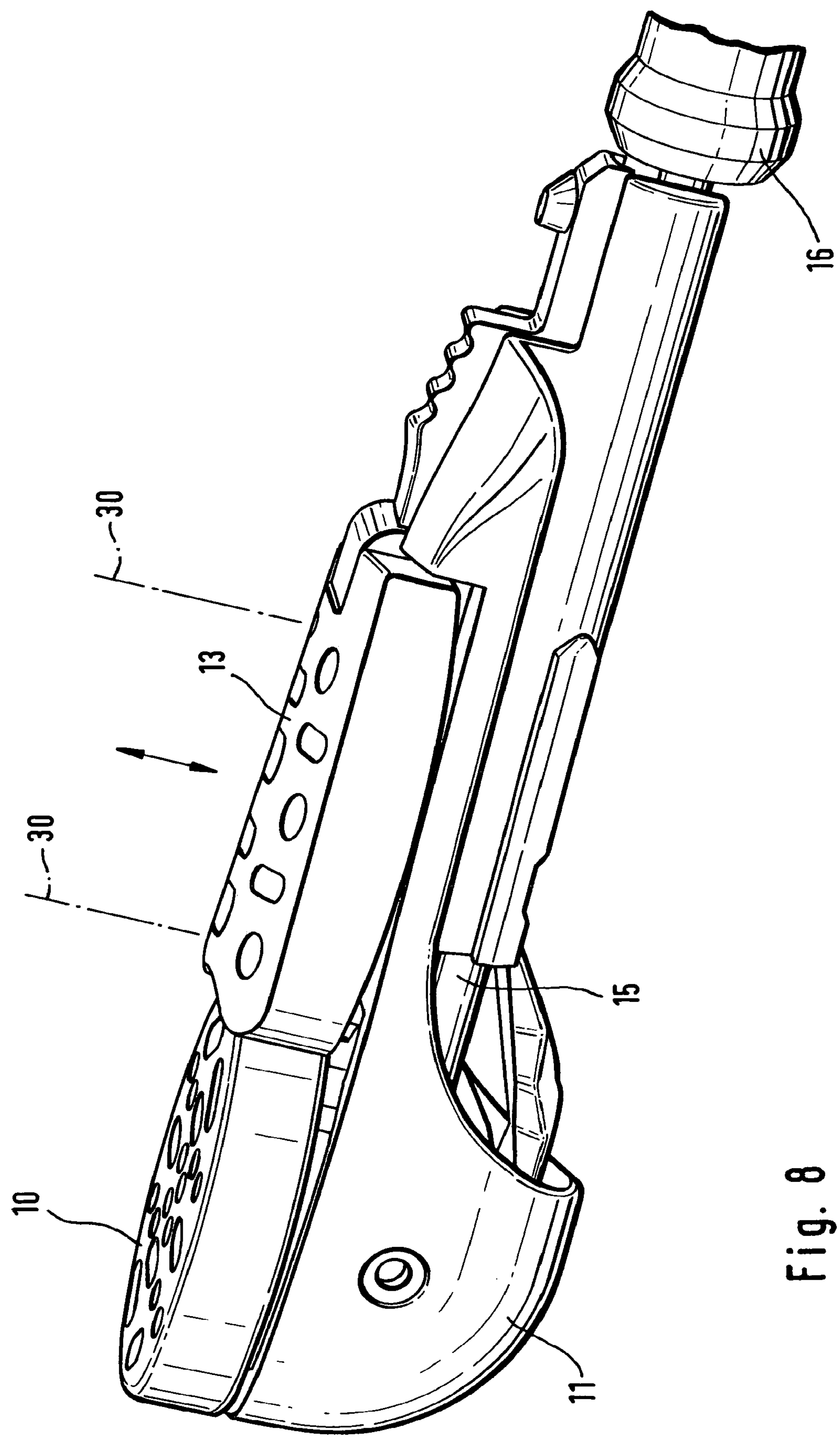
FIG. 8 shows a perspective view, in detail form, of a toothbrush head with two moveably mounted bristle carriers according to an alternative configuration of the invention, in which case the rear, additional bristle carrier is mounted such that it can be moved up and down about a translatory movement axis essentially parallel to the main bristle direction.
Figure 9:
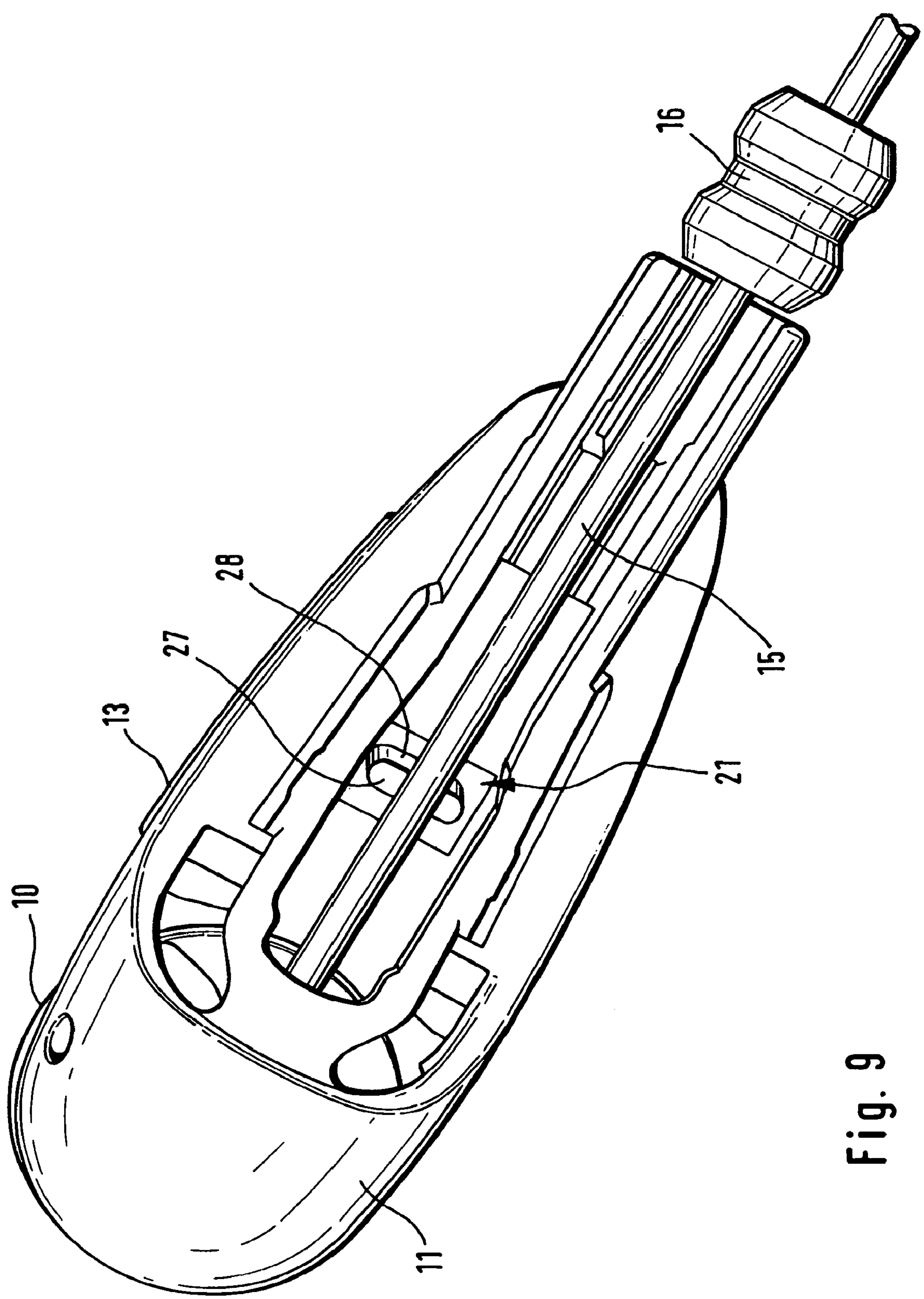
FIG. 9 shows a perspective view, in detail form, of the toothbrush head from FIG. 8 in a different viewing direction, this showing the drive mechanism for the two bristle carriers and, in particular, the coupling of the rear, additional bristle carrier to the drive rocker of the drive.

According to FIGS. 8 and 9, the additional bristle carrier 13 may also be guided such that it can be displaced in a translatory manner on the brush-head carrier 11. As FIG. 8 shows, the additional bristle carrier 13 may be guided along two movement axes 30 which extend essentially perpendicularly to the plane defined by the additional bristle carrier, or essentially parallel to the axis of rotation 12 of the bristle carrier 10. The sliding guide may be formed, for example, by a cylindrical bolt guide which is known per se. The sliding-guide axes 30 may be arranged, on the longitudinal centre plane of the toothbrush, in a rear and front edge section of the additional bristle carrier 13, as FIG. 8 shows. In accordance with the translatory movement capability of the additional bristle carrier 13, the latter can execute up and down stroke movements, with the result that the additional bristle arrangement 8 executes picking movements on the additional bristle carrier 13.

Here too, the stroke movement of the additional bristle carrier 13 is produced by a coupling to the drive rocker 15. As FIG. 9 shows, it is possible to provide, on an underside of the additional bristle carrier 13, a sliding surface 27 which extends transversely to the longitudinal direction of the toothbrush and is formed by the surface of a tappet 28 which projects in relation to the drive rocker 15. The tappet 28 is expediently arranged approximately centrally beneath the additional bristle arrangement and centrally between the movement axes 30, with the result that it is possible to produce a uniform force distribution and tilting-free movement. The teeth-cleaning reaction forces acting on the additional bristle arrangement 8 keep the sliding surface 27 in engagement with the drive rocker 15.

Figure 10:
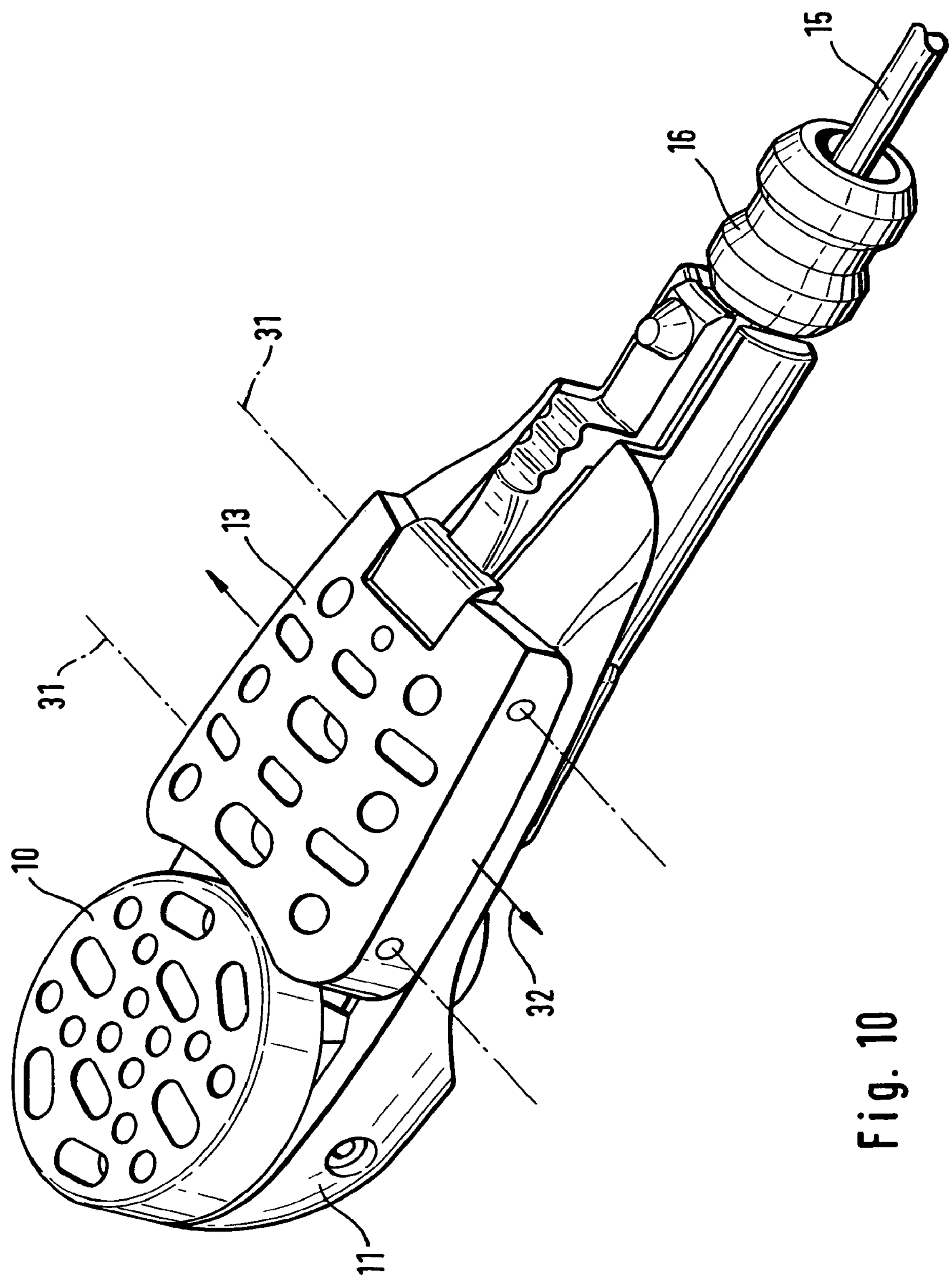
FIG. 10 shows a perspective view, in detail form, of a toothbrush head with two moveably mounted bristle carriers according to a further configuration of the invention, in which case the rear, additional bristle carrier is mounted such that it can be moved up and down about a translatory movement axis in a direction transverse to the longitudinal direction of the toothbrush and transverse to the main bristle direction.
Figure 11:
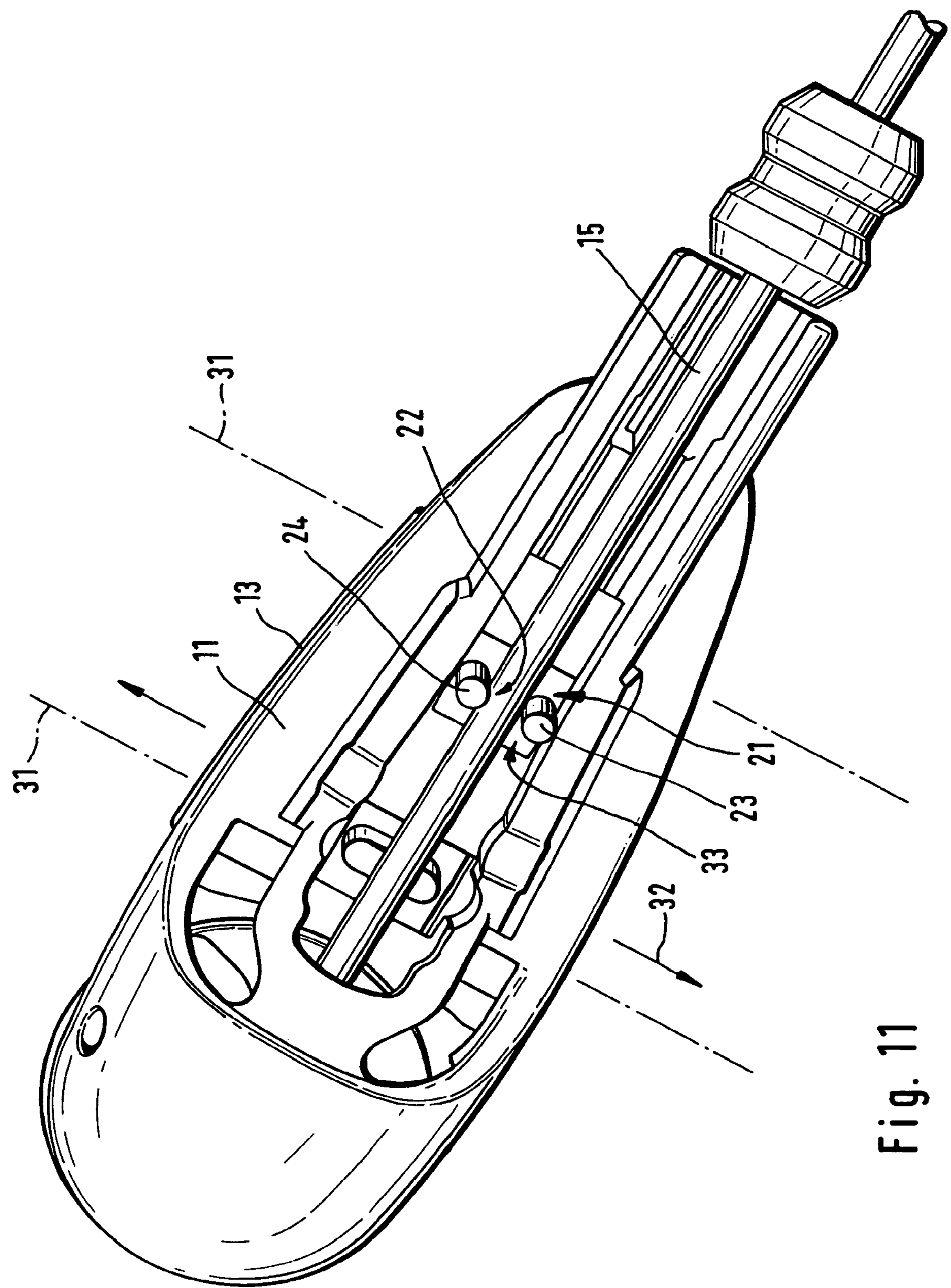
FIG. 11 shows a perspective view, in detail form, of the toothbrush head from FIG. 10 showing the drive mechanism for the two bristle carriers and, in particular, the coupling of the rear, additional bristle carrier to the drive rocker.

A further possible mounting for the additional bristle carrier 13 is shown in FIGS. 10 and 11. Here too, the additional bristle carrier 13 is mounted such that it can be displaced in a translatory manner on the brush-head carrier 11, to be precise along two parallel sliding-guide axes 31 which extend, in the plane defined by the additional bristle carrier 13, transversely to the longitudinal direction of the toothbrush, or to the axis of rotation 12 of the bristle carrier 10. As FIG. 10 shows, a rear end section of the additional bristle carrier 13, said section being directed towards the hand part 1, and an end section of the additional bristle carrier 13 which is directed towards the main bristle carrier 10 may be mounted by the abovementioned sliding guide. In this case, the additional bristle carrier 13 can execute transversely reciprocating movements in the lateral direction, as the arrow 32 illustrates.

In this case too, the translationally oscillating drive movement of the additional bristle carrier 13 is produced by the drive rocker 15. As FIG. 11 shows, the additional bristle carrier 13 is seated on the drive rocker 15 by means of a transverse guide 33. The transverse guide 33, in a manner similar to the configuration of FIGS. 2 and 3, is defined by two parallel post-like protrusions 23 and 24 which, between them, define a gap or a longitudinal cutout 22 which extends essentially perpendicularly to the plane of the additional bristle carrier 13. The drive rocker 15 can slide freely up and down in the vertical direction, i.e. in the longitudinal symmetry plane of the toothbrush, between the two protrusions 23 and 24. The drive movement of the drive rocker 15, however, is transmitted in a plane perpendicular thereto, i.e. in a plane parallel to the two sliding-guide axes 31, with the result that the additional bristle carrier 13 reciprocates in oscillation in the direction of the sliding-guide axes 31.

Figure 12:
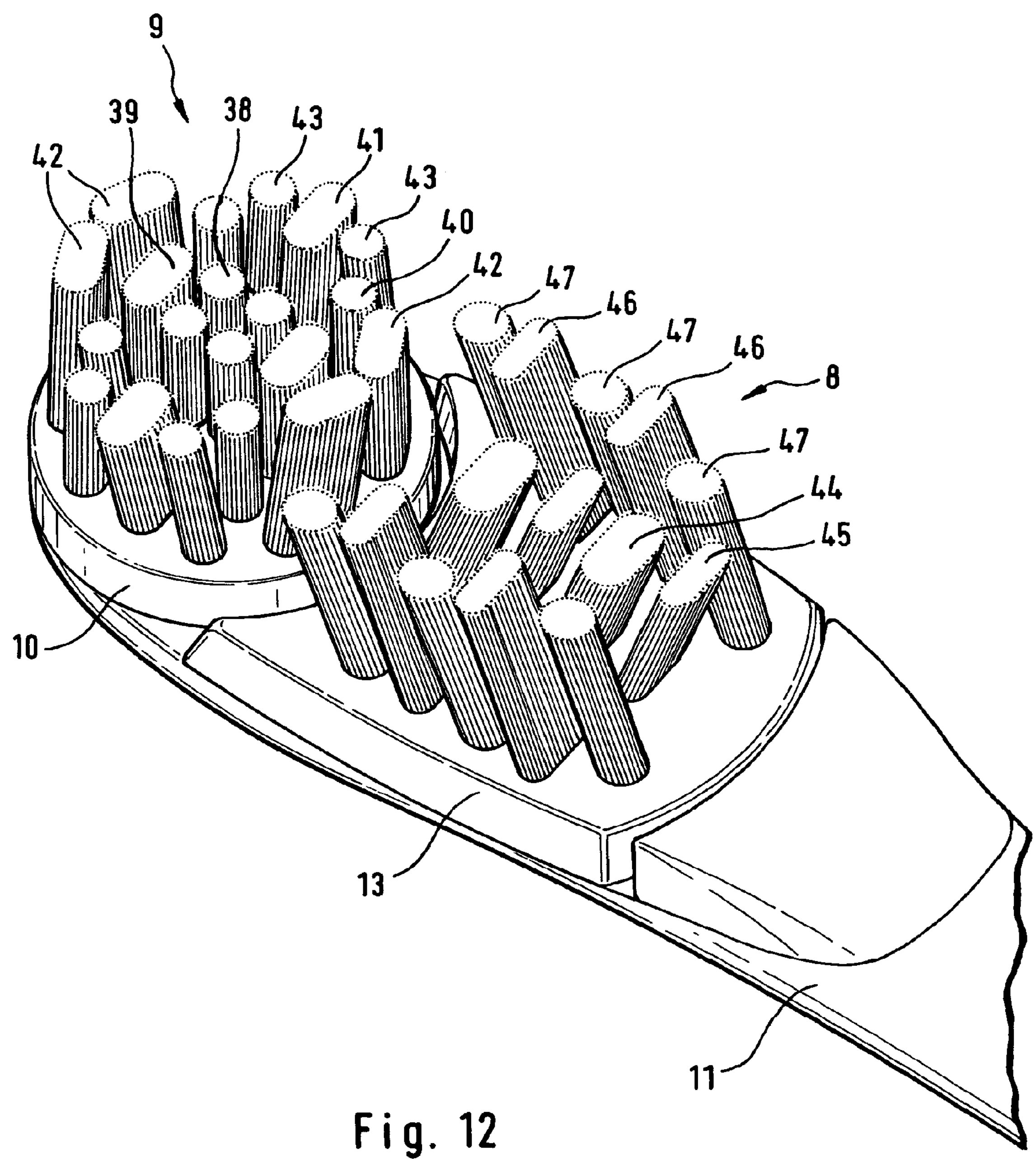
FIG. 12 shows a perspective view of a toothbrush head of the toothbrush from FIG. 1 showing the arrangement of the clusters of bristles on the two bristle carriers.

A preferred bristle covering of the two bristle carriers 10 and 13 is shown in FIGS. 12 to 14. It goes without saying that the bristle covering according to FIGS. 12 to 14 may be provided for each of the above described embodiments of the additional bristle carrier and/or the mounting thereof.

The main bristle arrangement 9, which can be driven in a rotationally oscillating manner, has an approximately circular-cylindrical outline overall and is formed by a plurality of clusters of bristles at different inclinations, of different heights and different cross sections.

As FIG. 12 and FIG. 13 show, central, first clusters of bristles 38 are arranged in the middle around the axis of rotation of the main bristle carrier. They extend perpendicularly to the plane defined by the bristle carrier 10 and have an approximately circular or slightly oval cross section. Four first clusters of bristles 38 are provided. They are located in the middle around the axis of rotation 12. Adjacent to the first cluster of bristles 38 are second clusters of bristles 39, which, when the bristle carrier 10 has not been rotated, are located on the longitudinal centre axis of the toothbrush and in front of, and behind, the first cluster of bristles 38, as seen in the longitudinal direction. As FIG. 12 shows, the second clusters of bristles 39 have an oval cross section with a longitudinal axis extending transversely to the longitudinal axis of the toothbrush. The second clusters of bristles 39 are likewise arranged perpendicularly to the plane defined by the bristle carrier 10. They are spaced apart from the axis of rotation 12 by a greater distance than the first clusters of bristles 38. The ratio of contour length to contour width is approximately two.

The rest of the clusters of bristles of the driven bristle arrangement are inclined, to be precise in different directions. The fourth clusters of bristles 40, which are arranged radially outside the first clusters of bristles 38, as it were on a second bristle-cluster ring, have an approximately circular cross section and are inclined radially outwards, i.e. their free working ends are further away from the axis of rotation of the bristle carrier than their fastening sections fastened on the bristle carrier 10. The angle of inclination is acute and less than 20°.

The third clusters of bristles 41 are likewise inclined radially outwards. However, they have an oval contour or an elongate cross section, the longitudinal axis of the cross section being oriented radially. The cross section of the third clusters of bristles is approximately twice to three times as long as it is wide. The third clusters of bristles 41 are seated radially outside the first clusters of bristles 38, adjacent to the latter, on a bristle-arrangement axis of symmetry running transversely to the longitudinal direction of the toothbrush.

The remaining clusters of bristles of the bristle arrangement 9 are likewise inclined, albeit in the circumferential direction about the axis of rotation 12. They form the outer edge or ring of the bristle arrangement 9.

The fifth clusters of bristles 42 have an oval contour or an elongate cross section, which is oriented approximately tangentially to the edge of the bristle carrier 10. In cross section, the clusters of bristles 42 are approximately twice to three times as long as they are wide. As FIG. 12 shows, the fifth clusters of bristles 42 are arranged in pairs in the region of the longitudinal axis of the toothbrush if the bristle arrangement 9 has not been rotated. They are inclined towards one another in pairs, with the result that their free working ends are closer together than their fastening sections anchored in the bristle carrier 10.

Finally, sixth clusters of bristles 43 are provided, these likewise being located on the outer edge of the bristle arrangement and being inclined in the circumferential direction about the axis of rotation 12. However, they have an approximately circular cross section and are arranged in pairs on both sides of the third clusters of bristles 41 and are likewise inclined towards the latter in opposite directions. The angles of inclination of the circumferentially inclined clusters of bristles 43 and 42 located on the outside are likewise acute and preferably less than 20° to the vertical through the plane defined by the bristle carrier 10.

As FIGS. 13 and 14 show, the clusters of bristles arranged on the moveable bristle carrier 10 have two lengths. The outer, fifth clusters of bristles 42, which are located right at the front and rear, as seen in the longitudinal direction, and of which the free ends are all located in a single plane, are longer than the rest of the clusters of bristles. The free ends of the fifth clusters of bristles 42 define a plane. The difference in height between the clusters of bristles is in the range of from 0.5 mm to 2.5 mm, preferably approximately 1.0 mm to 1.5 mm. In the configuration depicted, it is 1.2 mm.

The clusters of bristles of the additional bristle arrangement 8 likewise have different cross sections, in terms of contour and surface area, and, furthermore, are likewise inclined differently. Clusters of bristles of different lengths are also provided, as is yet to be described.

As FIG. 12 shows, roughly speaking three rows of clusters of bristles, all extending approximately in the longitudinal direction of the toothbrush, are provided in the additional bristle arrangement. The central row is located on the longitudinal centre axis of the additional bristle carrier 13, while the two outer rows are spaced apart transversely therefrom.

In the central row of bristles, all the clusters of bristles are inclined in the direction of the hand part 1. All the clusters of bristles have an elongate or oval cross section, but different cross-sectional surface areas. First clusters of bristles 44 of the fixed bristle arrangement 8 have an oval cross section, of which the longitudinal axis is approximately double the length of the transverse axis. The first clusters of bristles 44 alternate in the central row with clusters of bristles 45, which are referred to hereinbelow as fourth clusters of bristles and are likewise inclined rearwards in the direction of the hand part. The fourth clusters of bristles 45 likewise have an oval cross section, but are of considerably narrower design and have a smaller cross-sectional surface area than the first clusters of bristles. In accordance with the configuration depicted, the elongate cross section is approximately—roughly speaking—three times as long as it is wide. The length of the oval cross section here is slightly smaller than the length of the cross section of the first clusters of bristles 44.

The two outer rows of the clusters of bristles of the fixed bristle arrangement 8 comprise second and third clusters of bristles. Second clusters of bristles 46 have an oval cross section with a relatively narrow contour. The longitudinal axis of the elongate cross-sectional contour is approximately three times the width of the cross-sectional contour. The third clusters of bristles 47 have an approximately circular cross section, the diameter of the cross section being somewhat more than half the longitudinal axis of the cross section of the second clusters of bristles 46. As FIG. 12 shows, the third clusters of bristles 47 are spaced apart differently from the longitudinal centre axis of the brush head 2. The distance from the longitudinal centre axis decreases in the direction of the hand part 1. The third clusters of bristles 47, however, are still located one behind the other to the extent that their contour is located approximately behind the contour of the much wider, second clusters of bristles 46. The second and third clusters of bristles 46 and 47 are each inclined forwards, i.e. in the direction of the drivable bristle arrangement 9, at an acute angle, to be precise at an acute angle which may be preferably 12° to 15°. All the clusters of bristles of the additional bristle arrangement 8 are preferably inclined in the longitudinal centre plane of the brush head 2 or planes which are parallel thereto. In contrast, all the clusters of bristles of the main bristle arrangement 9 are inclined differently or in a different direction.

The clusters of bristles of the additional bristle arrangement 8 define two working planes, as FIG. 14 shows. The circular, third clusters of bristles 47 in the outer rows and the thicker, first clusters of bristles 44 in the central row are of shorter design and define, with their free working ends, a lower-level plane which coincides with the plane which is defined by the first, second, third, fourth and sixth clusters of bristles of the main bristle arrangement 9. A higher, second plane, in contrast, is defined by the longer, fourth clusters of bristles 45 in the central row and the second clusters of bristles 46 in the two outer rows. This higher plane coincides with the plane which is defined by the longer, fifth clusters of bristles of the main bristle arrangement 9. In the additional bristle arrangement 8, it is thus the case that the narrower, oval clusters of bristles are longer than the thicker clusters of bristles.

In contrast to the main bristle arrangement 9, the additional bristle arrangement 8, rather than having a circular contour, has an elongate contour overall which, at its end which is directed towards the rotating bristle arrangement 9, encloses the latter.

As FIG. 1 shows, the brush head 2 is fastened in a releasable manner on the brush tube 3. It can easily be drawn off from the brush tube 3, and pushed onto the same, in the axial direction. For this purpose, the brush-head carrier 11 has a fastening section 34 by means of which it can be pushed onto or into a corresponding fastening section 35 at the end of the brush tube 3. The two fastening sections 34 and 35 are both designed approximately in the form of half-shells in each case and supplement one another in a precisely fitting manner, with the result that, in the pushed-together state, they form a hollow profile which continues the brush tube 3.

In order to secure the brush head 2 in the axial direction on the hand part 1 and/or the brush tube 3, there is provided, between the brush-head carrier and the hand part 1, a latching device 36 which, when the brush head 2 is pushed on, latches automatically in the axial direction and, on the other hand, can be released again by radial pressure being applied to the brush tube 3 or the brush-head carrier. When the brush head 2 is pushed on, the drive rocker 15 is automatically coupled, at the same time, to the two moveable bristle carriers 10 and 13.

The invention claimed is:

1. A toothbrush head for an electric toothbrush, the toothbrush head comprising:

a brush-head carrier having an end configured to be releasably connected to a hand part of an electric toothbrush;

first and second bristle carriers attached to the brush-head carrier and bearing first and second sets of bristle tufts, respectively, each of the first and second bristle carriers being configured to be driven in a respective oscillation relative to the brush-head carrier in use, wherein at least one of the first and second sets of bristle tufts comprises a first bristle tuft which differs from a second bristle tuft with regard to at least one of bristle tuft cross section, bristle tuft length, bristle tuft inclination angle, and bristle stiffness, and wherein the second bristle carrier has two outer rows and at least one inner row, all said rows extending in a longitudinal direction of the toothbrush and comprising bristle tufts having oval-shaped cross-sections with a longer dimension oriented in a transverse direction relative to the longitudinal direction of the toothbrush, the bristle tufts in the outer rows being inclined in a first direction substantially parallel to the longitudinal direction of the brush, while the bristle tufts in the at least one inner row being inclined in a second direction opposite to the first direction.

2. The toothbrush head of claim 1, wherein bristle tufts of different inclination angle also differ from each other with respect to the bristle tuft cross section.

3. The toothbrush head of claim 1, wherein the first set of bristle tufts comprises at least one tuft of a different cross sectional shape than tufts of the second set of bristle tufts.

4. The toothbrush head of claim 1, wherein the first set of bristle tufts comprises at least one tuft of a different cross section than tufts of the second set of bristle tufts.

5. The toothbrush head of claim 1, wherein the first set of bristle tufts comprises at least one tuft of a different length than tufts of the second set of bristle tufts.

6. The toothbrush head of claim 1, wherein the first set of bristle tufts comprises at least one tuft extending at different bristle tuft inclination angle than tufts of the second set of bristles.

7. The toothbrush head of claim 6, wherein the tufts of different inclination angle also differ from each other with respect to the bristle tuft cross section.

8. The toothbrush head of claim 1 wherein each of the bristle carriers includes a drive-coupler extending from the bristle carrier and configured to engage a drive rocker when the toothbrush head is connected to a hand part.

9. The toothbrush head of claim 8 wherein at least one of the drive-couplers is affixed to one of the bristle carriers without a dedicated drive shaft, rocker, or rod.

10. The toothbrush head of claim 8 wherein at least one of the drive-couplers comprises cutouts and surfaces configured to engage the drive rocker when the toothbrush head is fitted onto the hand part.

11. The toothbrush head of claim 8, wherein at least one of the drive couplers is prestressed to engage a sliding surface with the drive rocker.

12. The toothbrush head of claim 1 wherein the first bristle carrier defines a movement axis transverse to a longitudinal axis of the toothbrush head.

13. The toothbrush head of claim 1 wherein the first bristle carrier is adapted to rotate about an axis arranged substantially perpendicularly to a longitudinal axis of the toothbrush head.

14. The toothbrush head of claim 1 wherein the first bristle carrier is adapted to rotate about an axis substantially parallel to a main bristle direction of the bristle arrangement disposed on the first bristle carrier.

15. The toothbrush head of claim 1, further comprising releasable fastening means for removable attachment of the brush-head carrier to the hand part.

16. The toothbrush head of claim 1 wherein the first set of bristle tufts extends from the first bristle carrier at multiple inclinations from a plane defined by an outer surface of the first bristle carrier, from which the first set of bristle tufts extend.

17. The toothbrush head of claim 1 wherein the second bristle carrier is configured to pivot about a pivot axis arranged approximately parallel to a plane defined by an outer face of the second bristle carrier.

18. The toothbrush head of claim 1 wherein the first set of bristle tufts have different cross sectional shapes, lengths, and angles of inclination than the second set of bristle tufts.

19. A toothbrush comprising a hand part containing an electric motor; and the toothbrush head of claim 1 coupled to the hand part.

20. A toothbrush head for an electric toothbrush, the toothbrush head comprising:

a brush-head carrier having an end configured to be releasably connected to a hand part of an electric toothbrush;

a main bristle carrier and an additional bristle carrier, each of the bristle carriers bearing a bristle arrangement, the bristle carriers being moveably attached to the brush-head carrier, each of the bristle carriers bearing a set of bristle tufts, at least one of the sets of bristle tufts comprising a first bristle tuft that differs from a second bristle tuft with regard to at least one of bristle tuft cross section, bristle tuft length, bristle tuft inclination angle, and bristle stiffness, and wherein the additional bristle carrier has two outer rows and at least one inner row, all said rows extending in a longitudinal direction of the toothbrush and comprising bristle tufts having oval-shaped cross-sections with a longer dimension oriented in a transverse direction relative to the longitudinal direction of the toothbrush, the bristle tufts in the outer rows being inclined in a first direction substantially parallel to the longitudinal direction of the brush, while the bristle tufts in the at least one inner row being inclined in a second direction opposite to the first direction; and one or more drive-couplers configured to engage the hand part when the toothbrush head is connected to the hand part, such that the hand part drives the main bristle carrier in rotational oscillation about a center axis and the additional bristle carrier in translational oscillation along a direction transverse to the toothbrush.

21. The toothbrush head of claim 20 wherein the first set of bristle tufts is differs from the second set of bristle tufts with regard to at least one of bristle tuft cross section, bristle tuft lengths, and bristle tuft inclination angle.

22. The toothbrush head of claim 20 or claim 21, wherein bristle tufts of different inclination angle also differ from each other with respect to the bristle tuft cross section.

* * * * *